(12) United States Patent
Narayanan et al.

(10) Patent No.: US 11,617,513 B2
(45) Date of Patent: Apr. 4, 2023

(54) MEASURING RAPID EYE MOVEMENT FOR CARDIORESPIRATORY MONITORING

(71) Applicant: INTERNATIONAL BUSINESS MACHINES CORPORATION, Armonk, NY (US)

(72) Inventors: Rajeev Narayanan, Briarcliff Manor, NY (US); Jenna Reinen, Greenwich, CT (US)

(73) Assignee: International Business Machines Corporation, Armonk, NY (US)

( * ) Notice: Subject to any disclaimer, the term of this patent is extended or adjusted under 35 U.S.C. 154(b) by 309 days.

(21) Appl. No.: 16/666,453

(22) Filed: Oct. 29, 2019

(65) Prior Publication Data

US 2021/0121080 A1     Apr. 29, 2021

(51) Int. Cl.
| | |
|---|---|
| *A61B 5/0205* | (2006.01) |
| *G16H 40/67* | (2018.01) |
| *G16H 50/20* | (2018.01) |
| *G16H 50/50* | (2018.01) |
| *A61B 5/11* | (2006.01) |
| *A61B 7/00* | (2006.01) |
| *A61B 5/145* | (2006.01) |
| *A61B 5/01* | (2006.01) |

(52) U.S. Cl.
CPC ............ *A61B 5/02055* (2013.01); *A61B 5/01* (2013.01); *A61B 5/1114* (2013.01); *A61B 5/14542* (2013.01); *A61B 7/003* (2013.01); *G16H 40/67* (2018.01); *G16H 50/20* (2018.01); *G16H 50/50* (2018.01); *A61B 2560/0214* (2013.01); *A61B 2562/0204* (2013.01); *A61B 2562/0261* (2013.01); *A61B 2562/0271* (2013.01)

(58) Field of Classification Search
CPC .... A61B 2560/0214; A61B 2562/0204; A61B 2562/0261; A61B 2562/0271; A61B 3/113; A61B 5/01; A61B 5/02055; A61B 5/1114; A61B 5/14542; A61B 5/4809; A61B 7/003; G16H 40/63; G16H 40/67; G16H 50/20; G16H 50/50; G16H 50/00–50/80
See application file for complete search history.

(56) References Cited

U.S. PATENT DOCUMENTS

| | | | |
|---|---|---|---|
| 4,863,259 A | * | 9/1989 | Schneider .............. A61B 3/113 351/210 |
| 8,025,404 B2 | | 9/2011 | Bolger |
| 8,162,479 B2 | | 4/2012 | Humphries |
| 8,721,081 B2 | * | 5/2014 | Martinez-Conde .......................... A61B 5/4082 351/209 |

(Continued)

FOREIGN PATENT DOCUMENTS

DE     102018204695 A1     4/2019

OTHER PUBLICATIONS

Mell et al., "The NIST Definition of Cloud Computing", National Institute of Standards and Technology, Special Publication 800-145, Sep. 2011, pp. 1-7.

*Primary Examiner* — Jonathan T Kuo
(74) *Attorney, Agent, or Firm* — Kristofer L. Haggerty

(57) ABSTRACT

A method, a structure, and a computer system for cardiorespiratory monitoring via rapid eye movement. The method comprises detecting eye movement of a user while asleep and determining whether the user is subject to a cardiorespiratory condition based on comparing the detected eye movement to a model.

13 Claims, 6 Drawing Sheets

(56) References Cited

U.S. PATENT DOCUMENTS

| | | | |
|---|---|---|---|
| 9,707,409 B2* | 7/2017 | Colbaugh | A61N 5/0618 |
| 9,814,430 B1 | 11/2017 | Berme | |
| 10,136,853 B2* | 11/2018 | Heinrich | A61B 7/00 |
| 2005/0110950 A1 | 5/2005 | Thorpe | |
| 2012/0238903 A1* | 9/2012 | Martinez-Conde | A61B 5/4082 |
| | | | 600/558 |
| 2013/0060306 A1* | 3/2013 | Colbauch | A61N 5/0618 |
| | | | 607/88 |
| 2014/0046184 A1* | 2/2014 | Heinrich | A61B 5/1128 |
| | | | 600/438 |
| 2016/0278633 A1 | 9/2016 | Kozlowski | |
| 2017/0294096 A1 | 10/2017 | Webb | |
| 2018/0160968 A1* | 6/2018 | Baltay | A61B 3/113 |
| 2019/0000349 A1* | 1/2019 | Narayan | A61B 7/003 |
| 2019/0000350 A1* | 1/2019 | Narayan | A61B 5/0826 |

* cited by examiner

MEASURING RAPID EYE MOVEMENT FOR CARDIORESPIRATORY MONITORING

BACKGROUND

The exemplary embodiments relate generally to cardiorespiratory monitoring, and more particularly to cardiorespiratory monitoring based on rapid eye movement.

Sleep stage abnormalities and eye movement disorders are often associated with poor health conditions, including strokes, cancer, Alzheimer's disease, Parkinson's disease, cardiovascular diseases, psychiatric diseases, cardiorespiratory diseases, and many others. For example, approximately 70% of the approximately 800,000 people affected annually by a stroke are also affected by an eye movement disorder and, according to the World Health Organization (WHO), strokes account for around 17 million deaths annually. The Center for Disease Control (CDC) estimates that strokes lead to 1 out of every 20 deaths, costing around USD 34 billion each year in the U.S. While a stroke patient may have good recovery if treated quickly, for example within 2-3 hours, a delay may cause long term brain damage and have debilitating impacts. Accordingly, early detection is key, yet 85% of strokes go unnoticed until too late, outside of the approximately 16-hour treatable window.

SUMMARY

The exemplary embodiments disclose a method, a structure, and a computer system for measuring rapid eye movement for cardiorespiratory monitoring. Exemplary embodiments include detecting eye movement of a user while asleep and determining whether the user is subject to a cardiorespiratory condition based on comparing the detected eye movement to a model. The exemplary embodiments may further include structure for detecting cardiorespiratory conditions based on rapid eye movement, the structure comprising one or more optical sensors, one or more strain gauge sensors, one or more microphones, one or more temperature sensors, and one or more batteries.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
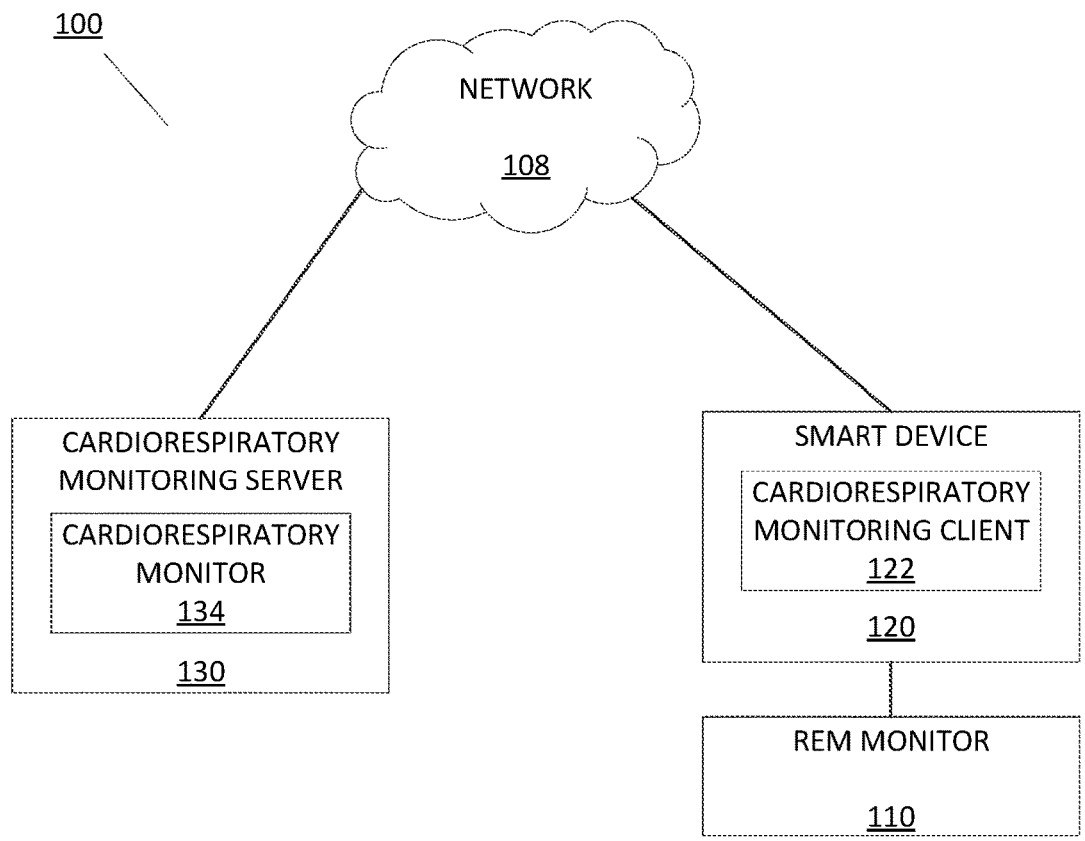
FIG. 1 depicts an exemplary schematic diagram of a cardiorespiratory monitoring system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

Sleep stage abnormalities and eye movement disorders are often associated with poor health conditions, including strokes, cancer, Alzheimer's disease, Parkinson's disease, cardiovascular diseases, psychiatric diseases, cardiorespiratory diseases, and many others. For example, approximately 70% of the approximately 800,000 people affected annually by a stroke are also affected by an eye movement disorder and, according to the World Health Organization (WHO), strokes account for around 17 million deaths annually. The Center for Disease Control (CDC) estimates that strokes lead to 1 out of every 20 deaths, costing around USD 34 billion each year in the U.S. While a stroke patient may have good recovery if treated quickly, for example within 2-3 hours, a delay may cause long term brain damage and have debilitating impacts. Accordingly, early detection is key, yet 85% of strokes go unnoticed until too late, outside of the approximately 16-hour treatable window.

Those who exhibit sleep stage abnormalies, for example stroke patients, may exhibit various conditions, including difficulty in maintaining normal ocular positions, disconjugate eye movement, difficulty moving the eyes appropriately, strabismus, saccadic eye movement, rapid eye movements that shift from one target to another, difficulty in smooth pursuit eye movements, etc. As previously mentioned, a large proportion of health conditions may be correlated with sleep cycle abnormalities. Sleep cycles are separated into stages that are defined by REM and non-REM brain waves. These stages are biologically distinct in terms of either slow-wave sleep and REM sleep, the latter of the two characterized by rapid eye movement, distinct brain activity, higher rate of dreaming, quicker pulse, and low muscle engagement. Sleep measurements often include measuring brainwaves, breathing, eye movements, leg movements, and EKG, with the gold standard encompassing at least all of the above. Moreover, during REM, autonomic dysregulation increases, and cardiac abnormalities may be worse, making autonomic dysregulation an important biomarker for health research.

Detecting rapid eye movement (REM) helps distinguish between sleep stages and is commonly measured through Electroencephalography (EEG), which utilizes bulky and uncomfortable equipment. Accelerometers may also be used to detect sleep stages, but such methods are notoriously inaccurate. Currently, detecting REM improves our ability to detect sleep abnormalities that predict health conditions such as a stroke, but both EEG and accelerometers used to identify these abnormalities have major drawbacks. There is a need for boosting an accuracy of sleep stage identification using wearable yet more accurate devices, which may increase the specificity and personalization needed to detect at-risk status for sleep disorders and cardiorespiratory conditions. Being able to detect REM stages as they differ from non-REM stages will contribute to this goal. Accordingly, a sensor-based rapid eye movement measuring device is needed to fill this deficiency.

Exemplary embodiments disclose a means for monitoring cardiorespiratory conditions based on rapid eye movement. Highlights of the exemplary embodiments include increased accuracy in monitoring cardiorespiratory health conditions, earlier detection of cardiorespiratory conditions, increased ease and comfort in monitoring cardiorespiratory conditions, reduced cost in monitoring cardiorespiratory conditions, and increased efficiency in monitoring cardiorespiratory conditions. Exemplary embodiments improve on existing solutions by gathering health data in a new, more accurate, and less invasive approach that implements data collection and analysis not considered by traditional approaches, as will be described in greater detail herein.

FIG. 1 depicts the cardiorespiratory monitoring system 100, in accordance with exemplary embodiments. According to the exemplary embodiments, the cardiorespiratory monitoring system 100 may include a rapid eye movement (REM) monitor 110, a smart device 120, and a cardiorespiratory monitoring server 130, which may be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted. For example, in embodiments, the cardiorespiratory monitor 134 and necessary components may be entirely stored on the REM monitor 110 or the smart device 120 for use locally without the need to connect to the network 108. The operations of the cardiorespiratory monitoring system 100 are described in greater detail herein.

In the exemplary embodiments, the network 108 may be a communication channel capable of transferring data between connected devices. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a Wi-Fi network, or a combination thereof. The network 108 may operate in frequencies including 2.4 gHz and 5 gHz internet, near-field communication, Z-Wave, Zigbee, etc. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices.

In exemplary embodiments, the REM monitor 110 may be a device capable of collecting data. In particular, the REM monitor 110 may be a wearable device such as an eye mask, headset, goggles, watch, headband, helmet, pillow, etc. In other embodiments, the REM monitor 110 may be a mountable or stationary device, such as a camera. In addition, the REM monitor 110 may include sensors such as one or more light emitting diodes (red, infrared, green, etc.), one or more optical sensors (red, infrared, green, etc.), one or more strain gauges (semiconductor/piezoresistance type, foil type, etc.), one or more temperature sensors, one or more microphones, one or more microcontrollers, one or more batteries, and one or more wireless communication adapters. The REM monitor 110 is described in greater detail with respect to FIGS. 2-5.

In exemplary embodiments, the smart device 120 includes a cardiorespiratory monitoring client 122, and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While the smart device 120 is shown as a single device, in other embodiments, the smart device 120 may be comprised of a cluster or plurality of computing devices, in a modular manner, etc., working together or working independently. The smart device 120 is described in greater detail as a hardware implementation with reference to FIG. 5, as part of a cloud implementation with reference to FIG. 6, and/or as utilizing functional abstraction layers for processing with reference to FIG. 7.

The cardiorespiratory monitoring client 124 may act as a client in a client-server relationship, and may be a software and/or hardware application capable of communicating with and providing a user interface for a user to interact with a server and other computing devices via the network 108. Moreover, in the example embodiment, the cardiorespiratory monitoring client 124 may be capable of transferring data from the smart device 120 to and from other devices via the network 108. In embodiments, the cardiorespiratory monitoring client 124 may utilize various wired and wireless connection protocols for data transmission and exchange, including Bluetooth, 2.4 gHz and 5 gHz internet, near-field communication, Z-Wave, Zigbee, etc. The cardiorespiratory monitoring client 124 is described in greater detail with respect to FIG. 2-5.

In the exemplary embodiments, the cardiorespiratory monitoring server 130 may include a cardiorespiratory monitor 134, and may act as a server in a client-server relationship with the cardiorespiratory monitoring client 124. The cardiorespiratory monitoring server 130 may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of receiving and sending data to and from other computing devices. While the cardiorespiratory monitoring server 130 is shown as a single device, in other embodiments, the cardiorespiratory monitoring server 130 may be comprised of a cluster or plurality of computing devices, working together or working independently. The cardiorespiratory monitoring server 130 is described in greater detail as a hardware implementation with reference to FIG. 5, as part of a cloud implementation with reference to FIG. 6, and/or as utilizing functional abstraction layers for processing with reference to FIG. 7.

In the exemplary embodiments, the cardiorespiratory monitor 134 may be a software and/or hardware program that may be capable of initiating an REM monitoring session. In addition, the cardiorespiratory monitor 134 may be capable of collecting optical sensor data, strain gauge sensor data, noise data, and temperature data. Moreover, the cardiorespiratory monitor 134 may be capable of applying a model to the collected data in order to determine whether a cardiorespiratory condition is detected. Based on determining that the respiratory condition is detected, the cardiorespiratory monitor 134 may be capable of taking action. Lastly, the cardiorespiratory monitor 134 may be capable of adjusting the models applied to the collected data. The cardiorespiratory monitor 134 is described in greater detail with reference to FIG. 2-5.

Figure 2:
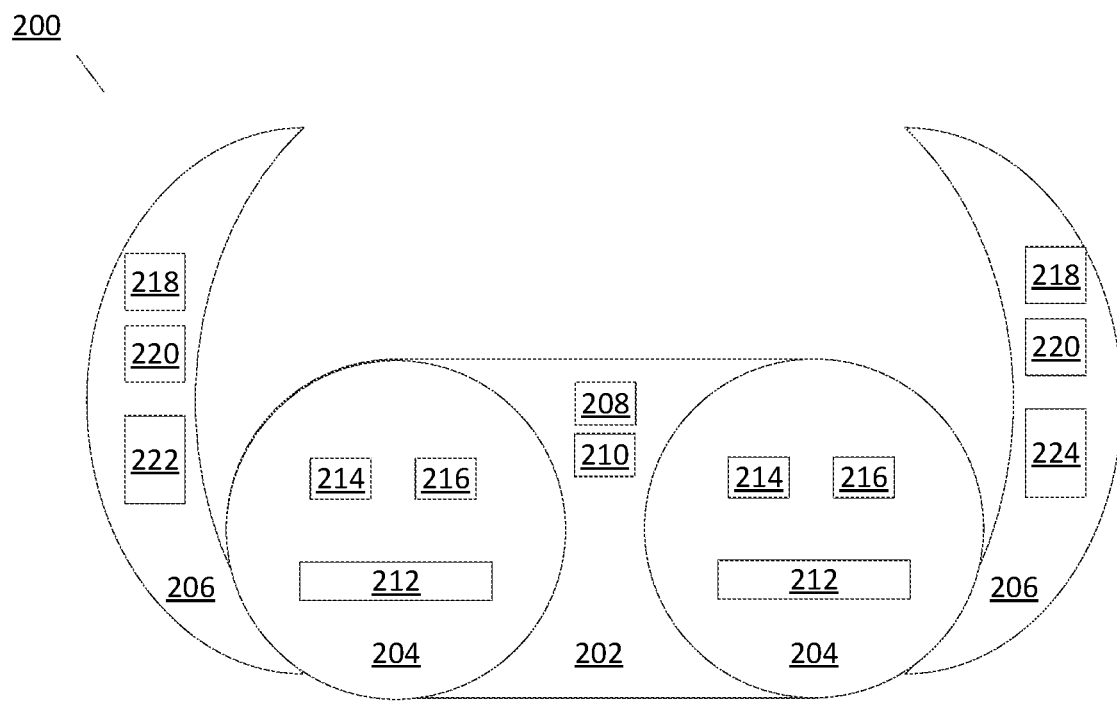
FIG. 2 depicts an exemplary schematic diagram 200 of a rapid eye movement (REM) monitor 110 of the cardiorespiratory monitoring system 100 in measuring rapid eye movement for cardiorespiratory monitoring, in accordance with the exemplary embodiments.

FIG. 2 depicts an exemplary schematic of a REM monitor 110 of the cardiorespiratory monitoring system 100, in accordance with the exemplary embodiments. In the example embodiment, the REM monitor 110 may comprise an eye mask 202, one or more eye patches 204, and one or more straps 206. In embodiments, the REM monitor 110 may be modular, and therefore components of the REM monitor 110 may be removed or replaced after a set period of time or use. For example, components housing temporary sensors, such as the one or more eye patches 204, may be disposable and be replaced ever several days/weeks/months. Moreover, positioning of the components within the REM monitor 110 may vary based on application. For example, batteries, microcontrollers, wireless adapters, and other components may be relocated from the one or more straps 206 or the eye mask 202 to different mounting locations based on application, fit, wearer, type of device, etc.

In embodiments, electrical components of the REM monitor 110 may be formed on an electronics substrate roughly 3 mm×3 mm, measured without an antenna which may be mounted to the REM monitor 110. The substrate may comprise films, flexible integrated wiring layers that include sensors, a micro controller, a Bluetooth adapter, and a battery (described in greater detail herein). The flexible electronic package wiring can use thinned metal layers/alloys of noble metals or conductive adhesive materials, such as thin Pt, Au, or composite layers of TiNiPt or TiNiAu. The cardiorespiratory monitor 134 may implement Carbon and Silver conductive adhesives, or Ti—Ni—Cu films with flex compatible designs with or without proper moisture barrier or packaging seals. Moreover, the cardiorespiratory monitor 134 may utilized thinned layers of polymer and SiOx-SiN repeating layers or thin polymer layers with Ti and/or SiN layers. Moreover, alternating ultra-thin layers of Ti and/or SiN and polymers with each layer being <20 nm to 50 nm may be repeated to create a flexible hermetic package of thickness typically <0.5 um to 50 um. The cardiorespiratory monitor 134 may implement bio-compatible polymers such as Topaz, liquid crystal dielectric, Polyimide, BCB, PET or other polymers, as well as apply surface coatings to seal packages with a Ti—Ni—Cu—Au layers or alternate compositions. In general, the components of the REM monitor 134 may be integrated into any suitable substrate. Detailed descriptions of the components follows.

In exemplary embodiments, the eye mask 202 includes a microphone 208 and a temperature sensor 210, and may be comprised of any material suitable for contact with human skin, namely the eyelids and area around the eyes. Accordingly, in embodiments, the eye mask 202 may be comprised of a material such as a fabric of cotton, polyester, etc., and may be secured to a face using one or more straps 206 such that the one or more eye patches 204 make contact with the eyelids of a user. In the example embodiment, the microphone 208 may be comprised of any microphone suitable for receiving audio of breathing, snoring, etc. For example, the microphone 208 may be a dynamic mic, a condenser mic, or a ribbon mic. Moreover, the temperature sensor 210 may be any temperature sensor suitable for detecting temperature of a person or environment. For example, the temperature sensor 210 may be a thermocouple, a thermistor, a thermometer, or a passive infrared sensor.

In the example embodiment, the one or more eye patches 204 may include one or more strain gauges 212, one or more infrared (IR) emitters 214, and one or more infrared (IR) detectors 216. In embodiments, the one or more strain gauges 212 may be semiconductor/piezoelectric strain gauges and may be configured in orientations such as quarter-, half-, and full-bridges. In other embodiments, the one or more strain gauges 212 may be foil, photoelectric, thin-film, etc. According to embodiments, the one or more IR emitters 214 may comprise a light emitting diode or other infrared emitting device. Moreover, the one or more infrared detectors 216 may be a thermal infrared detector, a photonic infrared detector, etc.

In the example embodiment, the one or more straps 206 may include one or more light emitting diodes (LED) 218, one or more light detectors 220, a microcontroller and batter 222, and a wireless adapter 224. In embodiments, the one or more LEDs 218 may be low-current, standard, and/or ultra-high-output, and emit light in a red, green, etc. color. Moreover, the one or more light detectors 220 may be comprise photoconductors (photoresistors), photovoltaic devices, photoresistor devices, photodiode devices, etc. The wireless adapter 224 may be configured for connecting to the network 108, and operate in Bluetooth, 2.4 gHz and 5 gHz internet, near-field communication, Z-Wave, Zigbee, etc.

Figure 3:
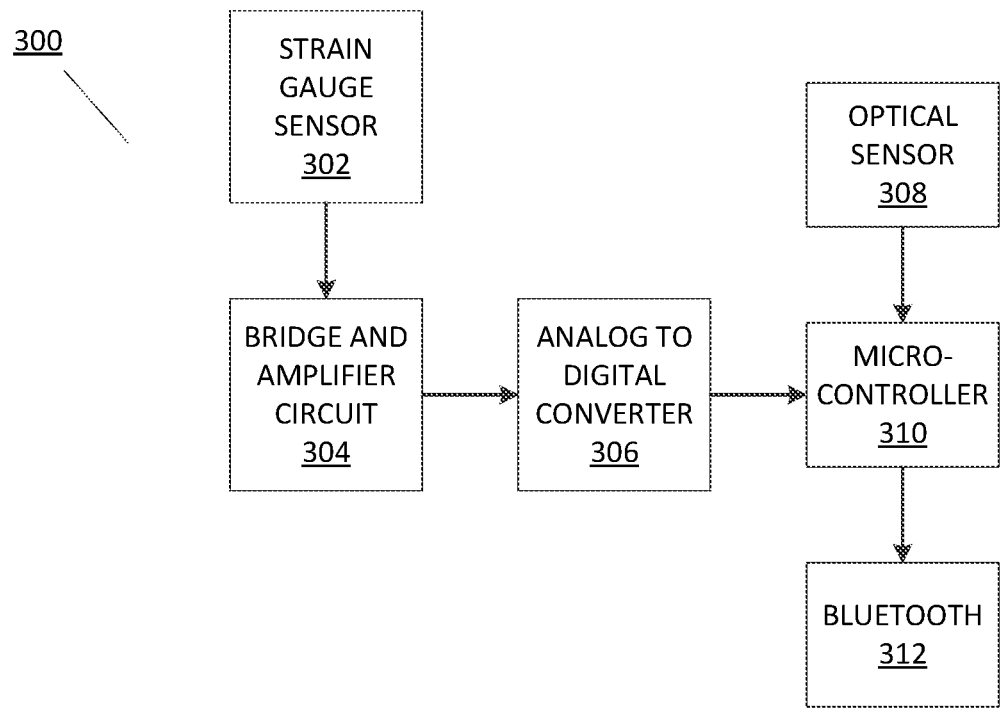
FIG. 3 depicts an exemplary flowchart 300 illustrating the processing of data gathered by the REM monitor 110 of the cardiorespiratory monitoring system 100 in measuring rapid eye movement for cardiorespiratory monitoring, in accordance with the exemplary embodiments.

FIG. 3 depicts an exemplary flowchart 300 illustrating the processing of data gathered by the REM monitor 110 of the cardiorespiratory monitoring system 100 in cardiorespiratory monitoring via measuring of rapid eye movement, in accordance with the exemplary embodiments.

The cardiorespiratory monitor 134 may receive strain gauge sensor data at step 302. In the example embodiment, the strain gauge sensor data may be collected by the one or more strain gauges 212 and received as electrical resistance generated during the deformation of the one or more strain gauges 212.

The cardiorespiratory monitor 134 may amplify the received strain gauge sensor data using a bridge and amplifier circuit at step 304.

At step 306, the cardiorespiratory monitor 134 may convert the amplified analog signal to a digital signal.

The cardiorespiratory monitor 134 may receive optical sensor data at step 308. Receiving the optical sensor data is described in greater detail with respect to FIG. 4.

At 310, the cardiorespiratory monitor 134 may receive the strain gauge sensor data and the optical sensor data for processing. Receiving the strain gauge sensor data is described in greater detail with respect to FIG. 4.

The cardiorespiratory monitor 134 may transmit the processed strain gauge and optical sensor data via the network 108, e.g., Bluetooth. The data may be transmitted to, for example, an electronic health record, a patient, a doctor, etc.

Figure 4:
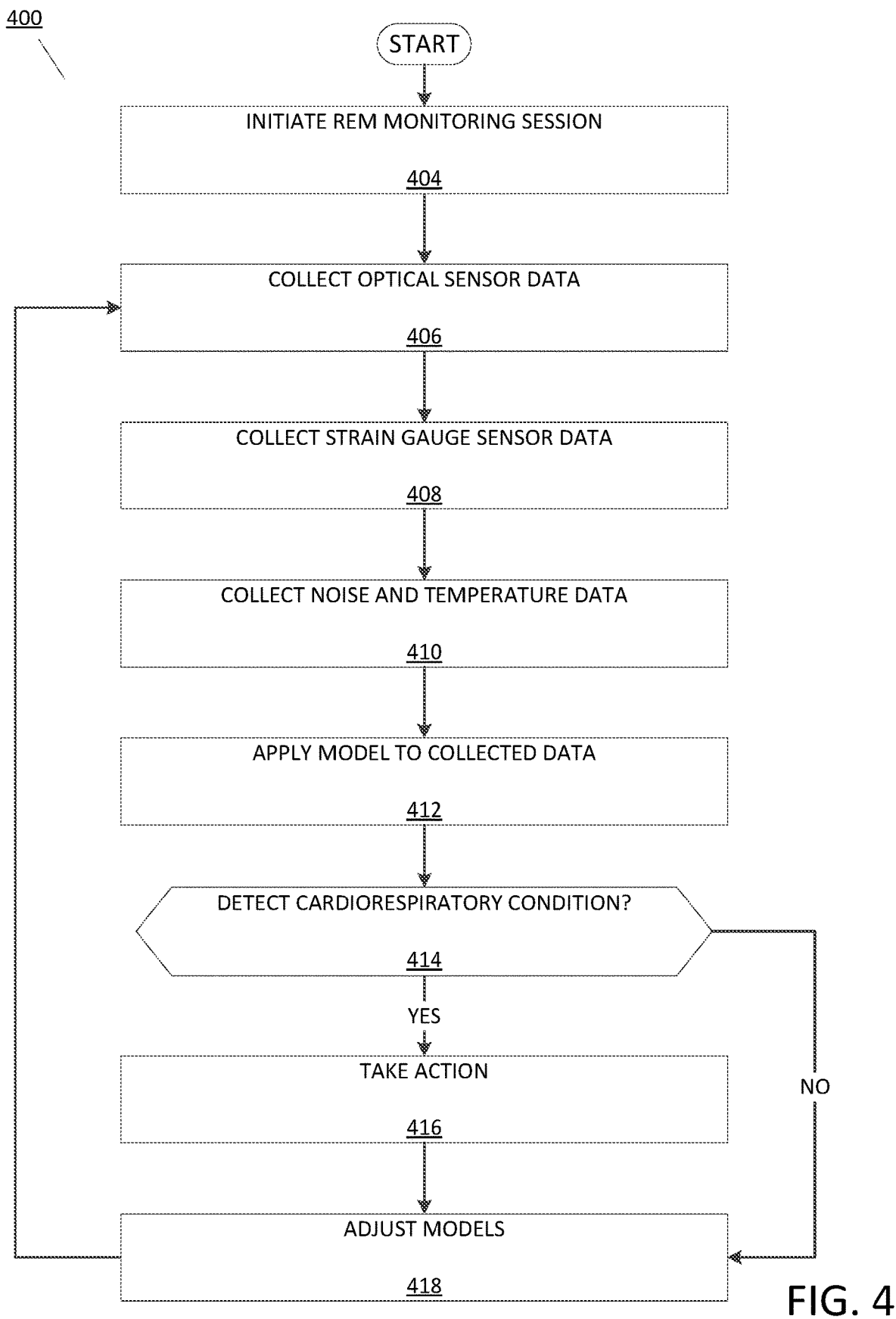
FIG. 4 depicts an exemplary flowchart 400 illustrating the operations of the cardiorespiratory monitor 134 of the cardiorespiratory monitoring system 100 in measuring rapid eye movement for cardiorespiratory monitoring, in accordance with the exemplary embodiments.

FIG. 4 depicts an exemplary flowchart 400 illustrating the operations the cardiorespiratory monitor 134 of the cardiorespiratory monitoring system 100 in cardiorespiratory monitoring based on REM, in accordance with the exemplary embodiments.

The cardiorespiratory monitor 134 may initiate an REM monitoring session (step 402). In the example embodiment, initiating the REM monitoring session may involve the cardiorespiratory monitor 134 receiving one or more user registrations and configuration/administrative settings via the cardiorespiratory monitoring client 122 and the network 108. In particular, the user registrations may include demographic information corresponding to a user of the REM monitor 110, such as a user name, gender, age, location, etc. In addition, the cardiorespiratory monitor 134 may further receive user health and diagnosis information, for example via an electronic health/medical record (EHR/EMR), one or more health tracking devices/programs, user input, etc. The cardiorespiratory monitor 134 may additionally receive user activity information, such a data from a fitness schedule, one or more fitness tracking devices/programs, user input, etc. Conversely, and in addition to tracking sleep autonomously, the cardiorespiratory monitor 134 may receive user sleep data via, for example, one or more sleep logs, sleep tracking devices/programs, user input, etc. In general, the cardiorespiratory monitor 134 may receive or extract any user profile data relevant to an identity, health, etc. of a user. The cardiorespiratory monitor 134 may be further configured to save and/or store the user registrations as profiles and reference, as well as add to, the profiles in subsequent REM monitoring sessions.

In addition to receiving the one or more user registrations, the cardiorespiratory monitor 134 may receive configuration settings (step 402 continued). In embodiments, the configuration settings may include configuring the smart device 120, the REM monitor 110, and/or an environment in which the cardiorespiratory monitoring system 100 is implemented. In embodiments where the REM monitor 110 communicates with the cardiorespiratory monitoring server 130 via the smart device 120, configuring the REM monitor 110 may include establishing secure network connections to the smart device 120 and the network 108. In other embodiments, configuring the REM monitor 110 may include establishing network connections directly to the network 108. In embodiments where the REM monitor 110 is implemented as a wearable (e.g., an eye mask), configuring the REM monitor 110 may include adjusting any settings relating to a fit of the REM monitor 110, including tightening any straps, modifying a distance between eye patches, adjusting a pressure of the eye patches, or otherwise adjusting the fit. Configuration of the REM monitor 110 may further include calibrating any settings, including those of one or more sensors implemented within the REM monitor 110 and illustrated by FIG. 2. For example, the REM monitor 110 may require adjustments including directing the one or more IR emitters 214 or the one or more LEDs 218 towards the eyelid of a user, or ensuring physical contact between one or more strain gauges 212 and eyelids of a user. In embodiments, configuration of the smart device 120 may include initiating connections to the REM monitor 110 and/or network 108, as well as downloading the cardiorespiratory monitoring client 122. In some embodiments, the cardiorespiratory monitor 134 may additionally receive an environment configuration. The environment configuration may include making connections to any devices or sensors within an atmosphere, such as external cameras, microphones, temperature sensors, humidity sensors, vibration sensors, gyroscopes, accelerometers, etc. not incorporated directly into the REM monitor 110.

With reference to an illustrative example, the cardiorespiratory monitor 134 receives user registration information of a 55 year-old male suffering from obstructive sleep apnea. In addition, the user connects the REM monitor 110 to his smart phone via Bluetooth, and the cardiorespiratory monitoring client 122 to the cardiorespiratory monitoring server 130 via WiFi.

The cardiorespiratory monitor 134 may collect optical sensor data (step 404). In the example embodiment, the cardiorespiratory monitor 134 may infer horizontal and vertical eyeball movement by emitting light towards an eyelid/eyeball from the one or more LEDs 218 and detecting reflections of the emitted light off of the eyelid/eyeball via the one or more IR detectors 216. By emitting the infrared light from a fixed position, the cardiorespiratory monitor 134 may detect and measure movement of the eyeball based on variations in the reflection of the emitted light. In the example embodiment, the cardiorespiratory monitor 134 may infer movement of the eyeball via spatial and temporal analysis of the reflection, with preferred resolutions of movement and elapsed time of at least 0.1 degrees and 1 ms, respectively. Moreover, the cardiorespiratory monitor 134 may configure the one or more IR emitters 214 to emit infrared (IR) light, as it is invisible to the naked eye and therefore won't be distracting to a sleeping user. In other embodiments, alternative means may be implemented to infer movement of an eyeball. For example, the REM monitor 134 may be equipped with an inward facing camera configured to capture movement of the eyeball/eyelid while in other embodiments, other contact and non-contact methods may be implemented.

The cardiorespiratory monitor 134 may further collect optical sensor data from the one or more LEDs 218 and the one or more light detectors 220 positioned on the one or more straps 206 (step 406 continued). In embodiments, the cardiorespiratory monitor 134 may utilize the optical sensor data gathered by the one or more light detectors 220 for monitoring activity of the temples of a user. In particular, the cardiorespiratory monitor 134 may collect optical sensor data of one or more veins within the temple in order to determine a peripheral capillary oxygen saturation (SpO2), or an amount of oxygen in the blood, which may be correlated with cardiorespiratory conditions. In the example embodiment, the one or more LEDs 218, as well as the corresponding one or more light detectors 220, may be configured for red, green, infrared, or other colors.

Furthering the earlier-introduced example, the cardiorespiratory monitor 134 collects optical sensor data by emitted an infrared light from a fixed light source in the direction of the user's eyes and detecting reflections of the infrared light to determine an eye movement rate (in degrees per second) of the user. In addition, the cardiorespiratory monitor 134 may further collect SpO2 levels of the user based on detecting the variance red light reflections off the temple of the user.

The cardiorespiratory monitor 134 may collect strain gauge sensor data (step 408). In the example embodiment, the cardiorespiratory monitor 134 may utilize the collected strain gauge data to infer horizontal and vertical eyeball movement via the one or more strain gauges 212, which make contact with the eyelids/eyeballs of the user. In the example embodiment, the cardiorespiratory monitor 134 is configured to detect movement of the eyeball via a change in electrical resistance experienced by the one or more strain gauges 212 as the movement deforms a shape of the one or more strain gauges 212. Based on a location and degree of electrical resistance variance, the cardiorespiratory monitor 134 is capable of deducing and quantifying a corresponding movement of the eyeball of the user. In the example embodiment, the one or more strain gauges 212 may be semiconductor strain gauges configured in quarter-, half-, and full-bridges. In other embodiments, the one or more strain gauges 212 may be comprised of other strain gauge types and configurations.

Returning to the example introduced above, the REM monitor 134 detects a change in electrical resistance of the one or more strain gauges incorporated into the REM monitor 110 and deduces an eye movement rate of the user The cardiorespiratory monitor 134 may collect noise and temperature data (step 410). In the example embodiment, the cardiorespiratory monitor 134 may infer that a user is sleeping, as well as which stage of sleep a user is in, via the microphone 208 and the temperature sensor 210. In particular, the cardiorespiratory monitor 134 may utilize the microphone 208 to collect noise data relating to breathing, coughing, snoring, etc., while utilizing the temperature sensor 210 to monitor body temperature. In the example embodiment, the cardiorespiratory monitor 134 may record peaks, valleys, patterns, anomalies, etc., of user breathing and temperature data over time for later analysis.

Continuing the example above, the cardiorespiratory monitor 134 records audio levels of the breathing pattern of the user. In addition, the cardiorespiratory monitor 134 records body temperatures of the user throughout the night.

The cardiorespiratory monitor 134 may apply a model to the collected data (step 412). In embodiments, the cardiorespiratory monitor 134 may monitor the health of a user, and in particular a chance of a cardiorespiratory condition, by comparing the collected optical sensor data, strain gauge sensor data, audio data, and temperature data to the one or more cardiorespiratory monitoring models. More specifically, the one or more cardiorespiratory monitoring models may be a set of algorithms that correlate a likelihood of a cardiorespiratory condition with one or more features. In the example embodiment, the features include eye movement, patterns/stage of sleep, snoring patterns, body temperature, etc., and the one or more cardiorespiratory monitoring models may correlate a frequency or magnitude of said features with a likelihood of an impending or current cardiorespiratory condition.

In some embodiments, the cardiorespiratory monitoring models may simply model a change in the features of a specific user over time, which may be an indication of an impending/current cardiorespiratory event/condition (step 412 continued). In such embodiments, the cardiorespiratory monitor 134 may determine a baseline of each of the aforementioned features by collecting data for a threshold period of time and identify deviations from the established baseline as indicators of a cardiorespiratory event/condition. In embodiments, the baseline may be established over a predefined course of time, or moving averages or other statistical techniques may be implemented to account for insignificant or expected changes over time. Moreover, the cardiorespiratory monitor 134 may be configured to detect variances from the established baseline that exceed a predefined absolute or relative threshold. In embodiments implementing the subjective analysis above, additional time may be required to establish the baselines, but the results may prove more personalized and subjective, and therefore more accurate.

In addition to a subjective analysis, the cardiorespiratory monitor 134 may be configured to apply a more objective analysis (step 412 continued). In embodiments, the cardiorespiratory monitor 134 may apply cardiorespiratory monitoring models that may be generalized to a population. In such embodiments, rather than comparing current user data to a previously-established baseline specific to that user, the cardiorespiratory monitor 134 may compare current user data to data of a population or demographic. There, the one or more cardiorespiratory models may be trained to look for features or feature values generally associated with cardiorespiratory conditions across most people. Such generalized characteristics may be previously trained based on supervised/unsupervised techniques, and in some embodiments may be based on data collected by the former, subjective method described above. In such embodiments, the cardiorespiratory monitor 134 is capable of aggregating and generalizing the feature characteristics and results of an entire population, thereby establishing maximums, minimums, relative changes, trends, etc. of an objective user. The cardiorespiratory monitoring models may capture these maximums, minimums, relative changes, trends, etc. of the features in the form of weights applied to features, thereby allowing the cardiorespiratory monitor 134 to apply such weights to new user data in predictive analysis.

Having applied the one or more cardiorespiratory monitoring models 132 to the collected features, the cardiorespiratory monitor 134 outputs a value, or confidence score, indicative of whether the user is currently or likely to suffer a cardiorespiratory condition.

With reference again to the example introduced above, the cardiorespiratory monitor 134 applies one or more models to the eye movement, audio levels, and temperature levels of the user in order to output a confidence score of 0.81.

The cardiorespiratory monitor 134 may detect whether a cardiorespiratory condition exists or is impending (decision 414). In the example embodiment, the cardiorespiratory monitor 134 determines whether a cardiorespiratory event or condition exists or is impending by comparing the determined confidence score to a predefined threshold. The predefined threshold may be based on the data of the specific user, or may be based on the data of many users. With regard to the latter, the data of the users may be categorized by demographic and health characteristics, including age, gender, health conditions, etc. In other embodiments, the cardiorespiratory monitor 134 may detect a cardiorespiratory event based on other phenomena, such as particular aspects of the data, such as a feature, exceeding a maximum/minimum threshold, etc.

With reference to the example above, the cardiorespiratory monitor 134 compares the confidence score of 81 with a threshold of 80 to determine that a cardiorespiratory condition exists or is impeding.

Based on detecting a cardiorespiratory condition (decision 414, "YES" branch), the cardiorespiratory monitor 134 may take action (step 416). In embodiments, the cardiorespiratory monitor 134 may take action by updating a corresponding user health record, immediately waking the user, alerting the user, alerting a doctor corresponding to the user, alerting a medical center/hospital, etc.

Returning to the example above, the cardiorespiratory monitor 134 records the measurements in an EMR of the patient and notifies the user that measurements from the previous night were consistent with those of stroke patients, recommending that the user see their doctor. The cardiorespiratory monitor 134 additionally alerts the doctor corresponding to the user of the increased levels.

The cardiorespiratory monitor 134 may adjust models (step 418). In embodiments, the cardiorespiratory monitor 134 may adjust models based on received feedback. The feedback may be received by a user, a doctor corresponding to the user, etc., and may modify weights associated with features within the cardiorespiratory models.

In the example above, if a doctor indicates that increased REM is normal for the user in light of other circumstances, the cardiorespiratory monitor 134 may reduce a weight or modify the confidence score threshold.

Figure 5:
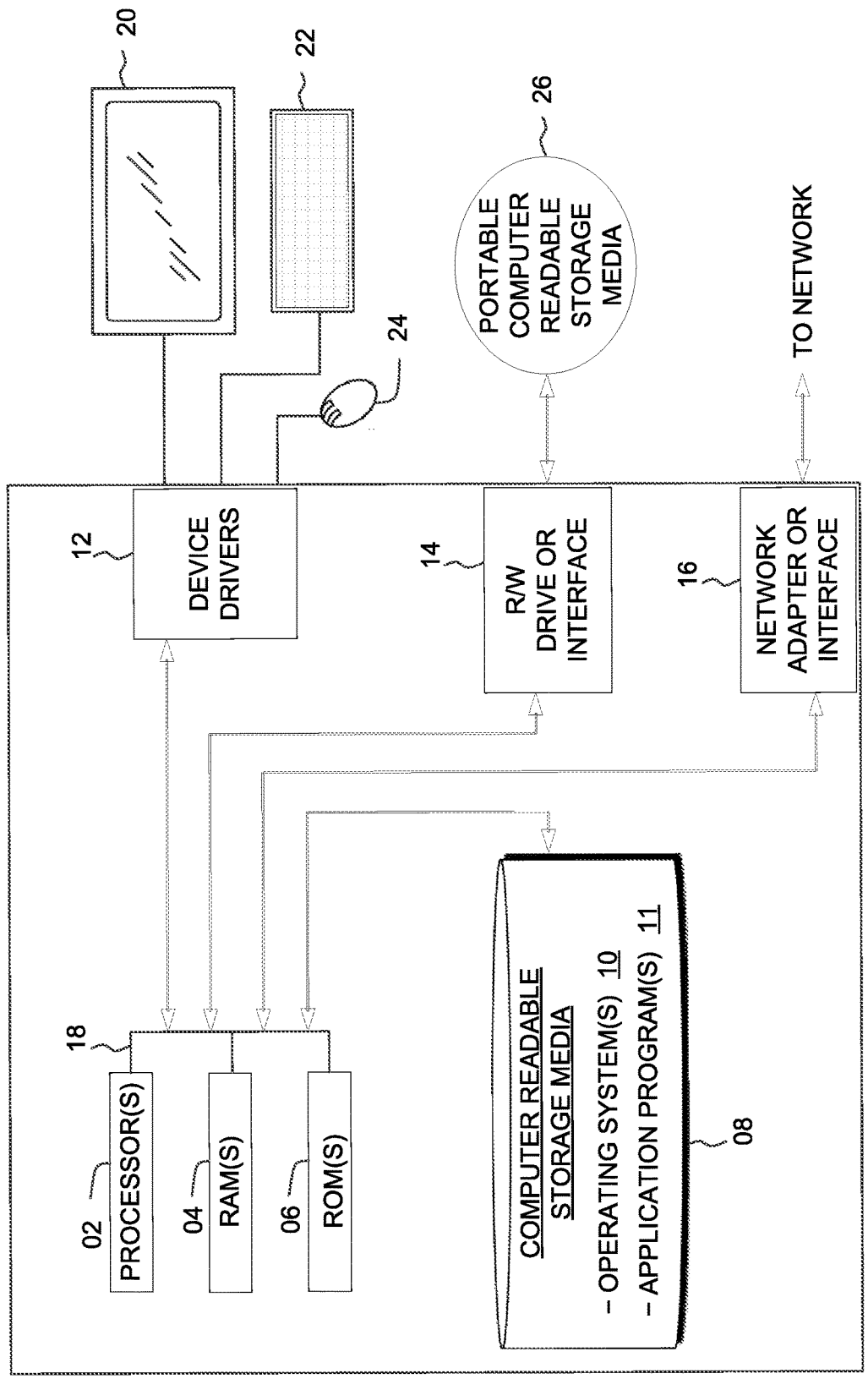
FIG. 5 depicts an exemplary block diagram depicting the hardware components of the cardiorespiratory monitoring system 100 of FIG. 1, in accordance with the exemplary embodiments.

FIG. 5 depicts a block diagram of devices within the cardiorespiratory monitoring system 100 of FIG. 1, in accordance with the exemplary embodiments. It should be appreciated that FIG. 5 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
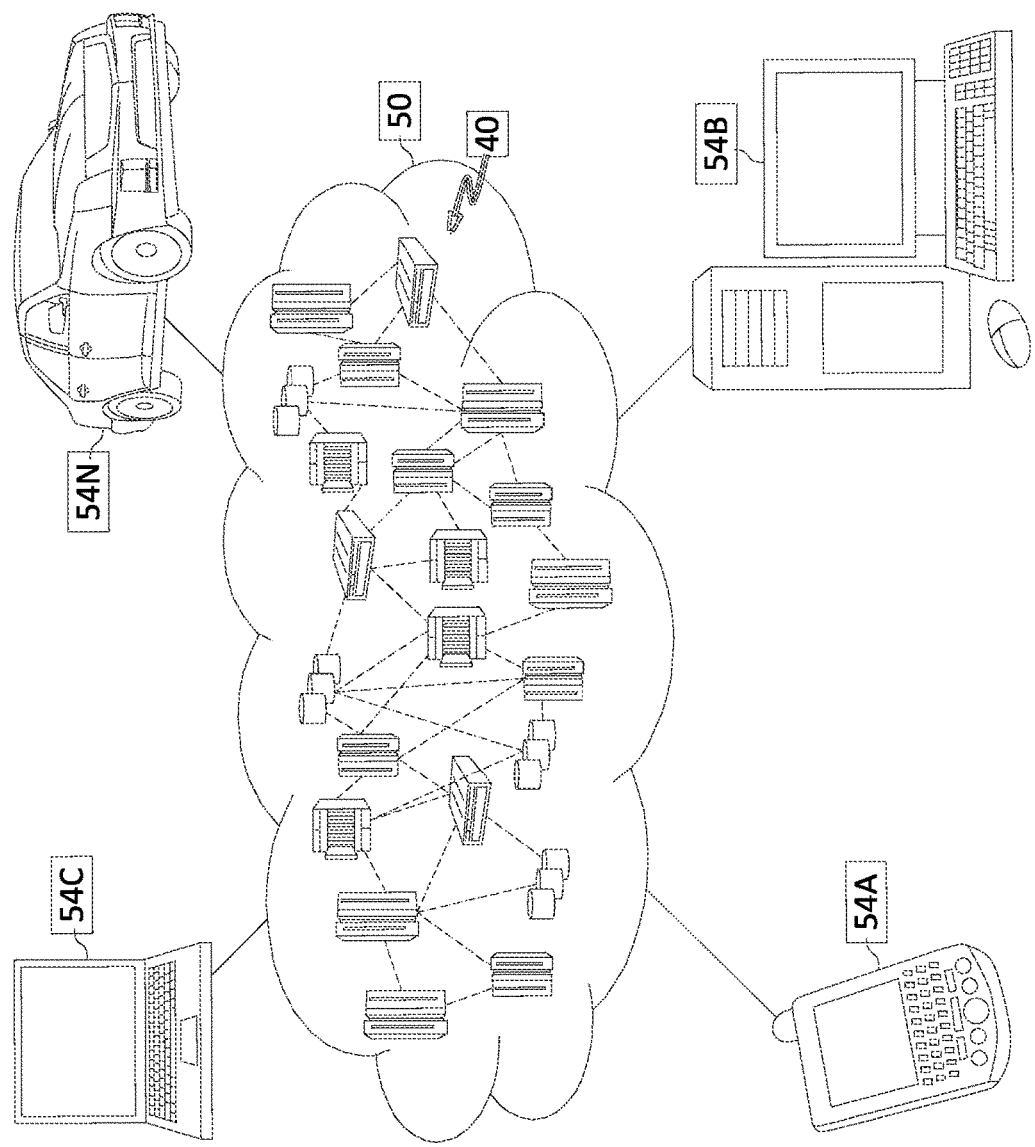
FIG. 6 depicts a cloud computing environment, in accordance with the exemplary embodiments.

Referring now to FIG. 6, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 40 and cloud computing environment 50 can communicate with any type of computerized device over any type of network and/or network addressable connection (e.g., using a web browser).

Figure 7:
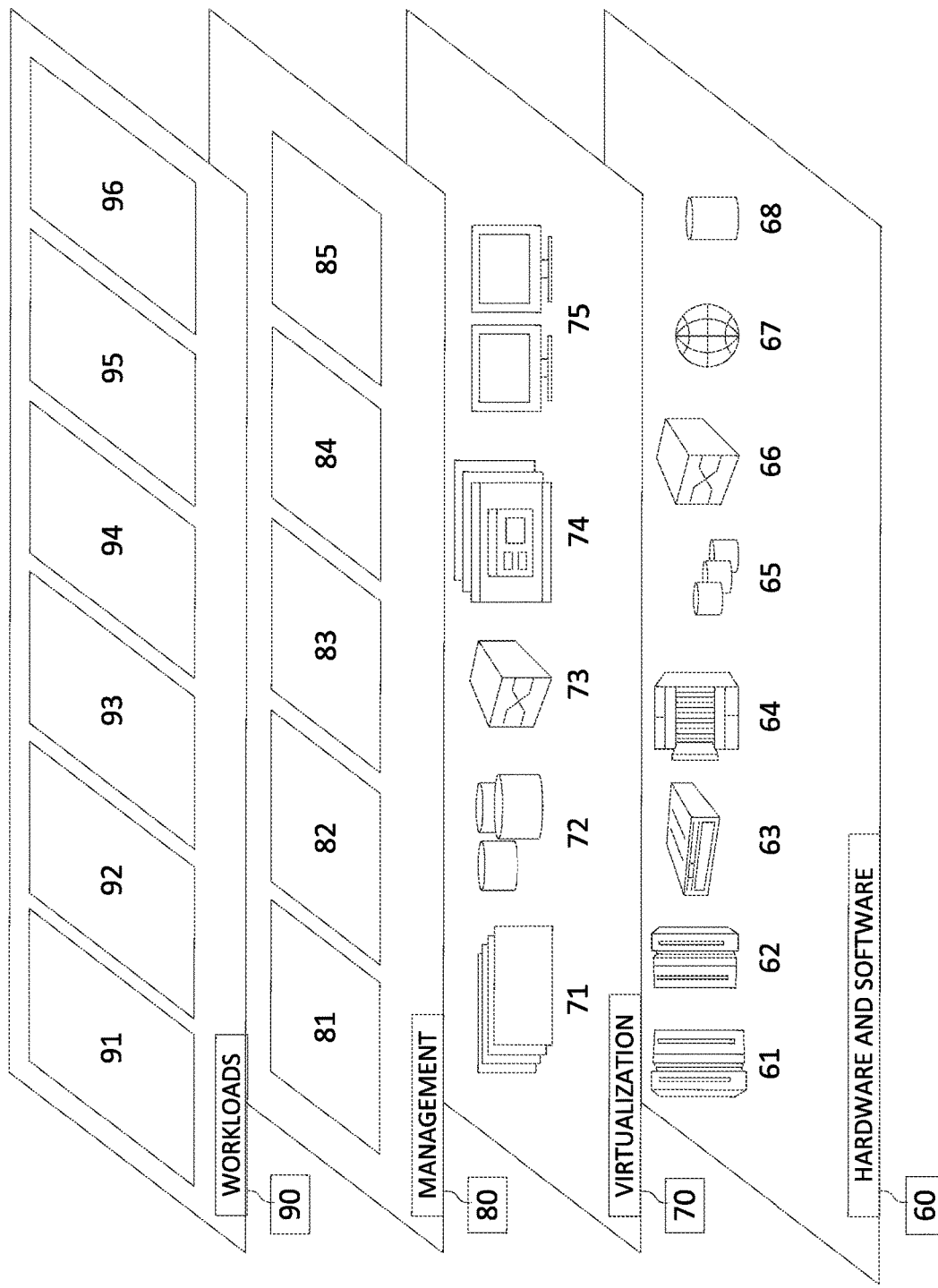
FIG. 7 depicts abstraction model layers, in accordance with the exemplary embodiments.

Referring now to FIG. 7, a set of functional abstraction layers provided by cloud computing environment 50 (FIG. 6) is shown. It should be understood in advance that the components, layers, and functions shown in FIG. 7 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and cardiorespiratory processing 96.

The exemplary embodiments may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for detecting cardiorespiratory conditions based on rapid eye movement, the method comprising:
    detecting eye movement of a user while asleep by one or more strain gauges within an eye mask worn by the user;
    determining a blood oxygen level corresponding to a vein within a temple of the user while asleep; and
    determining whether the user is subject to a cardiorespiratory condition based on comparing the eye movement and the blood oxygen level to a model, wherein the model correlates eyeball movement and blood oxygen level of the user with cardiorespiratory conditions of the user, and wherein the cardiorespiratory condition is a stroke.

2. The method of claim 1, wherein detecting eye movement of the user while asleep further comprises:
    emitting light from one or more light emitting diodes in a direction of an eye of the user; and
    detecting one or more reflections of the light off of an eye of the user.

3. The method of claim 1, further comprising:
    detecting snoring activity of the user while asleep, and wherein determining whether the user is subject to the cardiorespiratory condition is further based on comparing the detected snoring activity to the model.

4. The method of claim 1, further comprising:
    detecting a temperature of the user while asleep, and wherein determining whether the user is subject to the cardiorespiratory condition is further based on comparing the detected temperature to the model.

5. The method of claim 1, wherein the model determines whether the user is subject to the cardiorespiratory condition based on a comparison to historical user data.

6. The method of claim 1, wherein the model determines whether the user is subject to the cardiorespiratory condition based on a comparison to population data.

7. A structure for detecting a cardiorespiratory condition based on applying a model to measured rapid eye movement of a user, the cardiorespiratory condition a stoke, and the structure comprising an eye mask that includes:
    one or more optical sensors for determining a blood oxygen level corresponding to a vein within a temple of the user;
    one or more strain gauge sensors;
    one or more microphones;
    one or more temperature sensors; and
    one or more batteries.

8. A system for detecting cardiorespiratory conditions based on rapid eye movement, the system comprising:
    one or more optical sensors, one or more strain gauge sensors, one or more microphones, one or more temperature sensors, and one or more batteries; one or more computer processors, one or more computer-readable storage media, and program instructions stored on the one or more of the computer-readable storage media for execution by at least one of the one or more processors capable of performing a method, the method comprising:
    detecting eye movement of a user while asleep by one or more strain gauges within an eye mask worn by the user;
    determining a blood oxygen level corresponding to a vein within a temple of the user while asleep; and
    determining whether the user is subject to a cardiorespiratory condition based on comparing the eye movement and the blood oxygen level to a model, wherein the model correlates eyeball movement and blood oxygen level of the user with cardiorespiratory conditions of the user, and wherein the cardiorespiratory condition is a stroke.

9. The system of claim 8, wherein detecting eye movement of the user while asleep further comprises:
    emitting one or more light emitting diodes in a direction of an eye of the user; and
    detecting one or more reflections of the light emitting diodes off of the eye of the user.

10. The system of claim 8, further comprising:
    detecting snoring activity of the user while asleep, and wherein determining whether the user is subject to the cardiorespiratory condition is further based on comparing the detected snoring activity to the model.

11. The system of claim 8, further comprising:
    detecting a temperature of the user while asleep, and wherein determining whether the user is subject to the cardiorespiratory condition is further based on comparing the detected temperature to the model.

12. The system of claim 8, wherein the model determines whether the user is subject to the cardiorespiratory condition based on a comparison to historical user data.

13. The system of claim 8, wherein the model determines whether the user is subject to the cardiorespiratory condition based on a comparison to population data.

* * * * *